United States Patent [19]

Wasilewski

[11] Patent Number: 5,041,118
[45] Date of Patent: Aug. 20, 1991

[54] FEMORAL BROACH

[75] Inventor: Stanley A. Wasilewski, Randolph, N.J.

[73] Assignee: Implant Technology Inc., Secaucus, N.J.

[21] Appl. No.: 344,818

[22] Filed: Apr. 28, 1989

[51] Int. Cl.$^5$ .......................... A61F 5/04; A61F 2/30
[52] U.S. Cl. ........................................ 606/85; 623/16
[58] Field of Search ...................... 623/16, 18, 19, 20, 623/21, 22, 23; 606/85

[56] References Cited

U.S. PATENT DOCUMENTS

| | | | |
|---|---|---|---|
| 4,306,550 | 12/1981 | Forte | 606/85 |
| 4,552,136 | 11/1985 | Kenna | 623/16 |

OTHER PUBLICATIONS

"Implant Technology, Inc. LSF... Total Hip System", Product Information Catalog, Howmet Orthopaedic Products Facility, Howmet Turbine Components Corporation, 1986.
"Howmedica 1982 Annual Product Catalog", Howmedica, Ind. Orthopaedics Division, 1982.
"The Total System", Zimmer.

Primary Examiner—David J. Isabella
Attorney, Agent, or Firm—Nixon & Vanderhye

[57] ABSTRACT

A femoral broach for preparing an intramedullary canal for receiving a stem of a fermoral hip prosthesis is provided which comprises a body having posterior, anterior, medial and lateral faces, and divided generally into proximal and distal sections, the body having a shape corresponding substantially to the shape of the stem, the latter shape defined in part by a first curve along the posterior face, a second curve along the proximal portion of the anterior face, and a third curve along the distal portion of the anterior face. Each of the first, second and third curves are generated from different centers. A plurality of cutting teeth are provided on selected portions of said posterior, anterior, lateral and medial faces, the teeth including a first plurality of teeth extending substantially horizontally about the posterior, anterior, medial and lateral faces, and a second plurality of teeth extending substantially diagonally relative to the first plurality of teeth, about the posterior, anterior, medial and lateral faces. The body is also formed with a blank surface formed in the distal portion of the anterior and lateral faces, and a pair of generally vertically extending clearance channels formed in the blank surface in the lateral face. There is also provided a trunnion having a substantially U-shaped recess facing radially outwardly relative to the peripheral surface of the trunnion to facilitate mounting of the broach to a broach insertion tool.

14 Claims, 3 Drawing Sheets

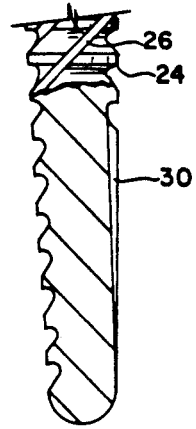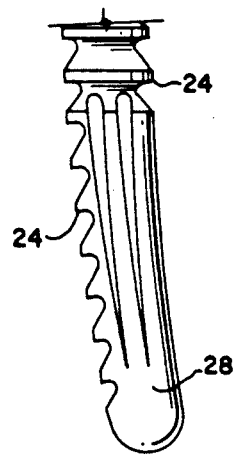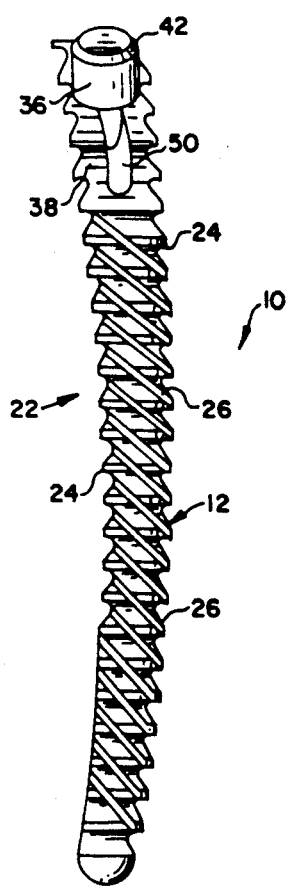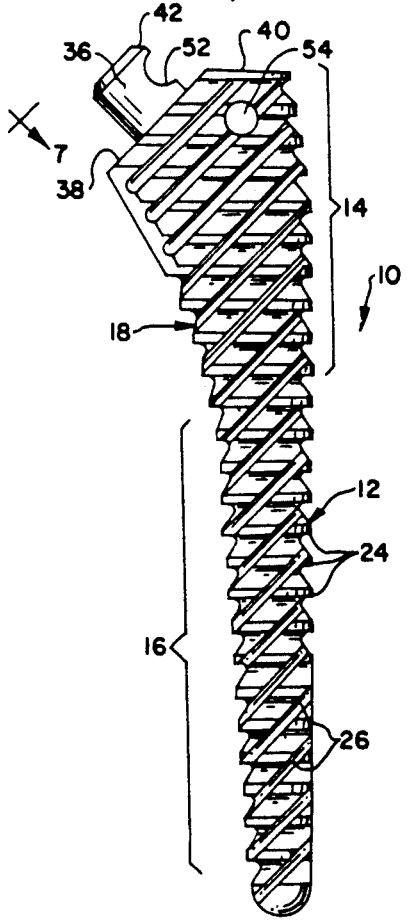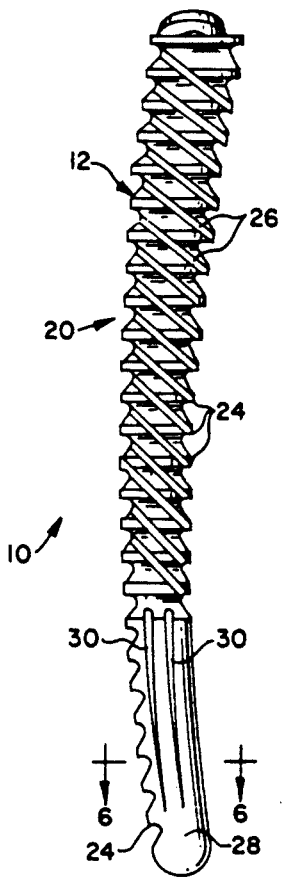

FEMORAL BROACH

The present invention relates to a femoral broach for preparing the intramedullary canal for receiving the stem component of a femoral hip prosthesis. More specifically, the invention relates to a femoral broach designed specifically for use with a femoral stem described in co-pending application Ser. No. 07/145,278 filed Jan. 19, 1988, the disclosure of which is incorporated herein by reference.

The preparation of the intramedullary canal for receiving a femoral stem prosthesis is a critical step in hip arthroplasty procedures. Accordingly, it is of utmost importance that the femoral broach utilized to prepare the canal be precision-formed to provide accurate, sharp cuts, and to facilitate removal of the removed tissue and bone chips as well.

Broaches, or rasps as they are sometimes called, are, of course, not new to the art (see, for example U.S. Pat. No. 4,522,136 issued Nov. 12, 1985). However, rasps of this type have not proven to be completely satisfactory insofar as they tend to effect a rasping or abrading (as opposed to a true broaching) action, so that precision bone cutting is not always obtained.

Accordingly, the present invention has for its principal object the provision of a femoral broach which is precision formed with horizontal and diagonal cutting teeth which are configured to the cut tissue, bone chips and other debris. The broach of this invention is also provided with a lengthwise curvature which is dimensionally matched, by computer comparison, to the associated femoral stem prosthesis, resulting in an intimate geometric match when the stem prosthesis is inserted into the prepared femur, accomplishing an effective, stable trochanteric locking mechanism without the undue insertion stress which is characteristic of oversized, press fit femoral prostheses which generally cause damaging microfractures in the femur.

In one exemplary embodiment, and as typical of prior art broaches, the femoral broach comprises a body which may be generally divided into a relatively wider and shorter proximal section, and a relatively narrower and longer distal section. The body portion may further be defined in terms of a posterior face, a lateral face, a medial face and an anterior face. In accordance with this invention, first and second pluralities of horizontal and diagonal cutting teeth, respectively, are provided about substantially the entirety of the four above mentioned faces with selected surface exceptions as noted further below.

The horizontal cutting teeth in accordance with an exemplary embodiment of the invention have essentially a 0° clearance angle for true broaching action and precise bone cutting. At the same time, the horizontal cutting teeth are provided with a 7° undercut angle which not only provides a clean precision cut, but also facilitates hard bone clearance and removal.

The diagonal cutting teeth extend at substantially a 45° angle relative to the horizontal cutting teeth, and serve the dual purpose of cutting and facilitating removal of cut material.

A lowermost portion of the distal section is provided with a generally blank, i.e. smooth, surface on the lateral and anterior faces of the broach. The blank surface on the lateral face is interrupted by a pair of longitudinally extending distant from a vertical centerline of the broach. The channels, which lie substantially perpendicular to the horizontal cutting teeth, extend over a distance of approximately 36 mm in one exemplary embodiment, and have depths which vary from an approximation of the depths of the diagonal and horizontal cutting teeth at the juncture of the channels and the cutting teeth, to an increasingly shallow depth in the distal direction. These channels are designed to augment bone cutting, clearance and removal, while protecting against violation of the lateral cortex, particularly during insertion of the broach into the canal.

In another aspect of the invention, the uppermost end of the proximal section of the broach is provided with a smooth surface on the medial face in order to prevent the broach from cutting into the proximal medial cortex during insertion.

In another aspect of the invention, the posterior and anterior faces of the femoral broach are curved along substantially the entire length of the broach, the curvature being defined by three distinct radii as will be described in greater detail below. As already noted, this curvature is substantially identical to the curvature in the associated femoral stem prosthesis.

The proximal section of the broach terminates at a top surface which includes a substantially horizontal portion, and an angled portion which extends downwardly toward the medial face. The angled surface mounts a substantially annular trunnion by which the broach can be fixed to a broach insertion tool, In accordance with one exemplary embodiment of the invention, the trunnion is formed with a radially outwardly facing U-shaped depression or slot. A groove is also provided in the top surface, extending along both the horizontal and angled portions and passing directly beneath the trunnion. The trunnion, its integrally formed cut-out portion, and the groove provide mounting surfaces for fixing the broach to the associated broach insertion tool.

The broach is also provided with a laterally extending bore adjacent the proximal end of the broach near the lateral face, and extending between the posterior and anterior faces. This bore provides an access location for emergency extraction in the event of trunnion failure or broach insertion tool failure.

Thus, the invention is broadly directed to a femoral broach which is provided for preparing an intramedullary canal for receiving a stem of a femoral hip prosthesis which comprises a body having posterior, anterior, medial and lateral faces, and divided generally into proximal and distal sections, the body having a shape corresponding substantially to the shape of the stem, the shape defined in part by a first curve along the posterior face, a second curve along the proximal portion of the anterior face, and a third curve along the distal portion of the anterior face, each of the first, second and third curves being generated from a different center; and a plurality of cutting teeth on selected portions of the posterior, anterior, lateral and medial faces.

The invention is also broadly directed to a femoral broach comprising a body having posterior, anterior, medial and lateral faces and divided generally into proximal and distal sections, the body having a shape corresponding substantially to the shape of an associated femoral stem prosthesis, and including a first plurality of teeth extending substantially horizontally about the body section including the posterior, anterior, medial and lateral faces; and a second plurality of teeth extending substantially diagonally relative to the first plurality of teeth, about the body section and including the posterior, anterior, medial and lateral faces.

The invention also broadly relates to a femoral broach for preparing an intramedullary canal for receiving a stem of a femoral hip prosthesis comprising a body section having posterior, anterior, medial and lateral faces, and divided generally into proximal and distal portions, the body section having a curvature corresponding substantially to the curvature of the stem, the body section further having a blank surface formed in the distal portion of the anterior and lateral faces, and a pair of generally vertically extending clearance channels formed in the blank surface in the lateral face.

The invention also broadly relates to a femoral broach for preparing an intramedullary canal for receiving a stem of a femoral hip prosthesis comprising a body section having posterior, anterior, lateral and medial faces; a plurality of teeth extending about selected portions of the posterior, anterior, lateral and medial faces; and a trunnion mounted on an angled proximal surface, the trunnion having a substantially U-shaped recess formed therein.

Additional objects, advantages and features of description which follows.

BRIEF DESCRIPTION OF THE DRAWINGS

FIG. 1 is a front or posterior view of a femoral broach in accordance with the invention;

FIG. 2 is a left or medial side view of the broach shown in FIG. 1;

FIG. 3 is a right or lateral side view of the broach shown in FIG. 1;

FIG. 4 is a detail of the lateral face shown in FIG. 3;

FIG. 5 is a partial cut away of the distal portion of the broach shown in FIG. 1;

DETAILED DESCRIPTION OF THE DRAWINGS

Figure 7:
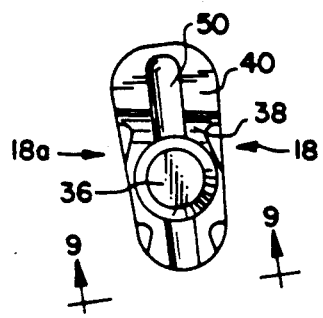
FIG. 7 is a top plan view of the broach taken along line 7—7 of FIG. 1.
Figure 6:
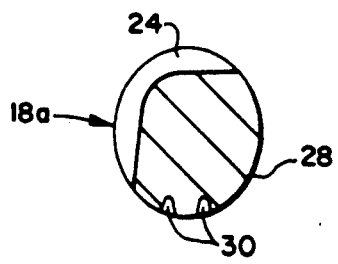
FIG. 6 is a section taken along the line 6—6 of FIG. 3.

Referring to FIGS. 1-3, the broach 10 comprises a body portion 12 which includes a relatively wider and shorter proximal section 14, and a relatively narrower and longer distal section 16. The broach is further defined in terms of a posterior face 18 (FIG. 1), a lateral face 20 (FIG. 3), a medial face 22 (FIG. 2), and an anterior face 18a (shown partially in FIGS. 6 and 7) which is opposite and similar to the posterior face.

Formed about substantially the entire body section 12, with two notable exceptions as explained below, are a first plurality of horizontal cutting teeth 24 which are designed to remove cancellous tissue and bone when the broach is forcibly inserted into the intramedullary canal.

Also formed within the body section, extending at substantially 45° relative to the horizontal teeth, across the posterior face 18, anterior face 18a, lateral face 20, and medial face 22 are a second plurality of diagonal cutting teeth 26 which extend through the cutting teeth 24 and which, in addition to their cutting function, serve to aid in the removal of tissue and bone chips as the broach is inserted and subsequently removed from the intramedullary canal.

The lower end portion of the distal section 16 is formed with a generally blank surface 28 on the lateral face 20 and posterior face 18a (see FIG. 6) interrupted on the lateral face by a pair of longitudinally extending clearing channels 30. These channels are located substantially equidistant from the vertical center line of the broach, and, in one exemplary embodiment, extend approximately 36 mm in length, from the distal terminus of the horizontal cutting teeth 24 and diagonal cutting teeth 26 to within 1 mm of the distal tip of the broach. The depth of these channels approximates the depth of the diagonal and horizontal cutting teeth at the uppermost ends of the channels, but becomes increasingly shallow in the distal direction. Channels 30 are designed to augment bone cutting clearance and removal, while protecting against violation of the lateral cortex, particularly during insertion of the broach into the canal. The blanked out surface 28 also directs the broach nominally posteriorly during insertion and away from the anterior cortex. This design insures that the cavity is prepared in a manner such that the prosthesis is inserted reproducibly into a neutral position, as viewed anterior to posterior, and that the distal tip of the prosthesis does not impinge on the anterior cortex.

The uppermost or proximal portion of the medial face is similarly provided with a smooth surface portion 29 which protects the medial cortex when the broach is fully inserted into the canal.

Figure 10:
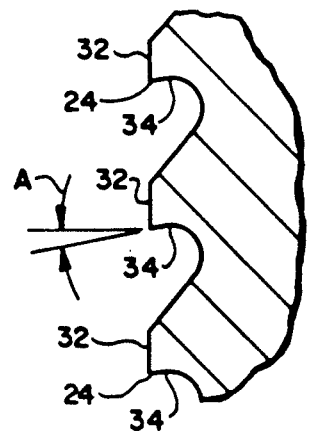
FIG. 10 is a partial detail taken from FIG. 1, showing the horizontal cutting teeth configuration.

With reference now to FIG. 10, the horizontal cutting teeth 24 include substantially vertical surface portions 32 which thereby define a clearance angle of 0° for true broaching action and precise bone cutting, as opposed to prior art cutting teeth where surfaces corresponding to those shown at 32 extend upwardly and radially inwardly to define a positive clearance angle (relative to vertical), and which result in a rasping or abrading rather than true broaching action.

The horizontal cutting teeth 24 in accordance with this invention are also formed with a 7° undercut angle, designated angle A in FIG. 10. The undercut, defined by the angle made by surface 34 relative to horizontal, provides a clean, precision "sculpture") cut, and facilitates hard bone (38-42 Rockwell) clearance and removal.

Figure 11:
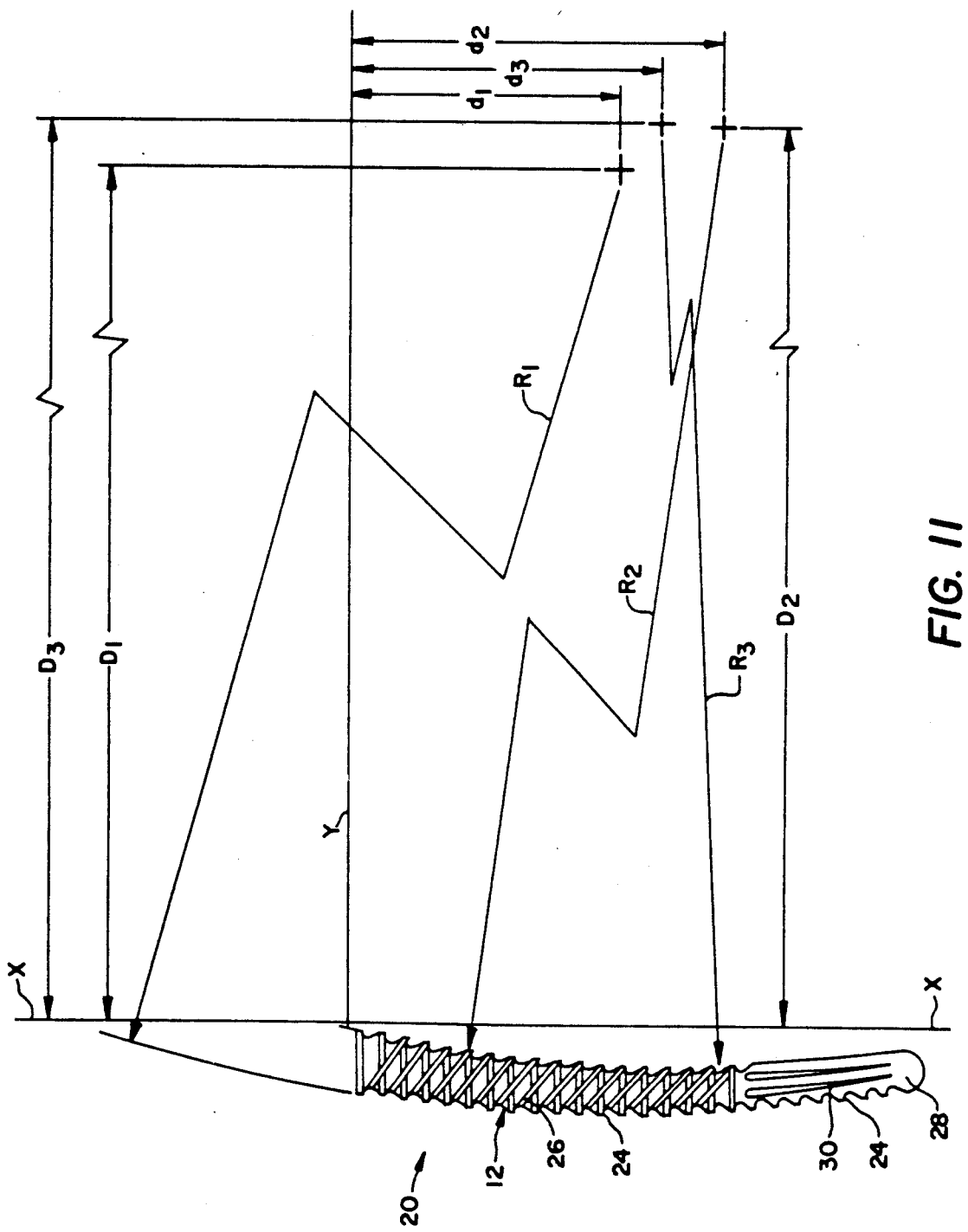
FIG. 11 is a lateral view as shown in FIG. 3, but illustrating the various radii which define the curvature of the broach.

Viewed from the lateral or medial faces, and as shown in FIG. 3 (lateral view), the broach is curved along its length, substantially identically to the corresponding curve in the femoral stem prosthesis (achieved by computer comparison) as described in applicant's co-pending application Ser. No. 07/145,278. Specifically, the lengthwise curvature is defined by three distinct arcuate surfaces. Thus, the posterior surface is defined by a radius $R_1$; the proximal portion of the anterior surface is defined by a radius $R_2$; and the distal portion of the anterior surface is defined by a radius $R_3$. In one exemplary embodiment, $R_1$, $R_2$ and $R_3$ are equal, and preferably 14.1732 inches. However, the respective centers from which each radius is generated are located in different positions. For example, as viewed in FIG. 11, horizontal distance D from a vertical line X (extending parallel to the longitudinal axis of the stem) laterally to the center point of each radius preferably as follows:

$D_1 = 13.4792$ inches; $D_2 = 13.8356$ inches; and $D_3 = 13.8484$ inches. At the same time, vertical distances from a horizontal line Y (extending perpendicular to the longitudinal axis of the stem and to line X) to the center point of each radius is preferably follows: $d_1 = 2.2640$ inches; $d_2 = 3.0750$ inches; and $d_3 = 2.7425$ inches.

It has been determined by Tullos et al. that the curvature of the femur, measured from the midline of the femoral neck to an area two to three centimeters distal to the lesser trochanter, dictates the curvature dimensions provided above in order to anatomically match the femoral canal.

The free end of the proximal portion of the broach is provided with a trunnion 36 projecting outwardly from a substantially flat, angled surface 38 which is contiguous with, and extends at substantially 45° relative to, a substantially flat top surface 40. The trunnion 36 is cylindrical in shape, with a chamferred edge 42 about its upper peripheral surface. An elongated stem 44 projects below the trunnion and serves to mount the trunnion for flush engagement with surface 38. The stem 44 fits within a bore 46 provided in the body of the broach, and is held there by a transversely oriented locking pin 48. within surfaces 38, 40 and across the bore 46. In addition, the trunnion 36 is formed with a U-shaped cut-out or depression 52, facing radially outwardly from the peripheral surface of the trunnion, toward the top surface 40. The groove 50, trunnion 36 and cut-out 52 provide surfaces for engaging cooperating surfaces on a broach insertion tool of the type mentioned above. The U-shaped cut-out 52 not only facilitates connection to the tool, but it is also believed that this design extends the fatigue life of the trunnion.

Figure 8:
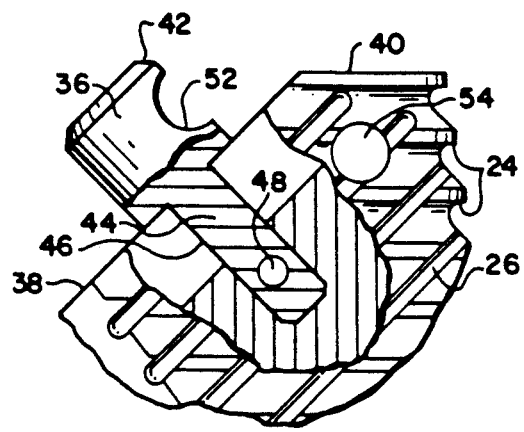
FIG. 8 is a detail of the broach taken from FIG. 1, partially cut away to illustrate mounting of a trunnion on the broach.
Figure 9:
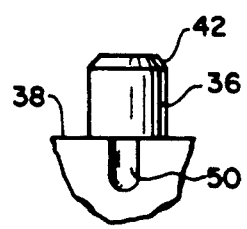
FIG. 9 is a partial section taken along the line 9—9 of FIG. 7.

Also with reference to FIG. 8, a bore 54 located near the lateral face 20, extends laterally through the broach, from the anterior face to the posterior face, and provides an emergency extraction port by which means may be connected to the broach to aid in its removal from the intramedullary canal in the event of trunnion and/or broach insertion tool failure.

The femoral broach of this invention is constructed of a biocompatible metal material, preferably 17-4 stainless steel. Both the trunnion and cross pin are preferably 416 stainless steel. The broach is cast with the horizontal teeth 24 on all four faces but with the diagonal teeth 26 on only the anterior and posterior faces. Upon removal from the mold, the diagonal teeth 26 on the medial and lateral faces are provided by machining.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A femoral broach for preparing an intramedullary canal for receiving a stem of a femoral hip prosthesis comprising:
   a body having a longitudinal axis and posterior, anterior, medial and lateral faces, said body divided generally into proximal and distal sections, the body having a shape defined in part by a first lengthwise curve along and substantially coextensive with the posterior face, a second lengthwise curve along the proximal section of the anterior face, and a third lengthwise curve along the distal section of the anterior face, each of said first, second and third curves being generated from a different center; and
   a plurality of cutting teeth on selected portions of said posterior, anterior, lateral and medial faces.

2. A femoral broach as defined in claim 1 wherein each of said centers is offset lengthwise with respect to each other, relative to the longitudinal axis of the broach.

3. A femoral broach as defined in claim 2 wherein each of said curves has a radius substantially identical to each other.

4. A femoral broach as defined in claim 3 wherein each radius is equal to about 14 inches.

5. A femoral broach as defined in claim 2 wherein said first curve has a center offset vertically toward the proximal section relative to said second and third curves.

6. A femoral broach as defined in claim 2 wherein said first curve has a center offset horizontally toward said posterior and anterior faces relative to said second and third curves.

7. A femoral broach as defined in claim 2 wherein said second and third curves are not offset horizontally with respect to each other.

8. A femoral broach as defined in claim 1 wherein the body section comprises cast stainless steel.

9. A femoral broach as defined in claim 1 and wherein said plurality of cutting teeth include a first plurality of teeth extending substantially horizontally about the posterior, anterior, medial and lateral faces;
   a second plurality of teeth extending substantially diagonally relative to said first plurality of teeth, about the posterior, anterior, medial and lateral faces.

10. A femoral broach as defined in claim 1 and wherein said body includes a blank surface formed in the distal portion of said anterior and lateral faces, and a pair of generally vertically extending clearance channels formed in said blank surface in said lateral face.

11. A femoral broach as defined in claim 9 and wherein said body includes a blank surface formed in the distal portion of said anterior and lateral faces, and a pair of generally vertically extending clearance channels formed in said blank surface in said lateral face.

12. A femoral broach as defined in claim 1 and including a trunnion mounted on an angled proximal surface, the trunnion having a substantially U-shaped recess formed therein.

13. A femoral broach as defined in claim 9 and including a trunnion mounted on an angled proximal surface, the trunnion having a substantially U-shaped recess formed therein.

14. A femoral broach as defined in claim 11 and including a trunnion mounted on an angled proximal surface, the trunnion having a substantially U-shaped recess formed therein.

* * * * *